US00PP34549P2

(12) United States Plant Patent
van Dijk

(10) Patent No.: US PP34,549 P2
(45) Date of Patent: Sep. 6, 2022

(54) ***HYDRANGEA* PLANT NAMED 'HIMEA'**

(50) Latin Name: *Hydrangea macrophylla*
Varietal Denomination: 'HIMEA'

(71) Applicant: Roy Robin van Dijk, De Lier (NL)

(72) Inventor: Roy Robin van Dijk, De Lier (NL)

(73) Assignee: HI BREEDING B.V., DeLier (NL)

( * ) Notice: Subject to any disclaimer, the term of this patent is extended or adjusted under 35 U.S.C. 154(b) by 0 days.

(21) Appl. No.: 17/688,804

(22) Filed: Mar. 7, 2022

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Hydrangea* plant named 'HIMEA', characterized by its compact, upright and broadly outwardly spreading and mounding plant habit; moderately vigorous and moderate growth rate; freely branching habit; strong and sturdy stems; dark green-colored leaves; freely flowering habit; large and dense inflorescences with vivid purplish red-colored sterile flowers; and good post-production longevity.

3 Drawing Sheets

Figure 1:
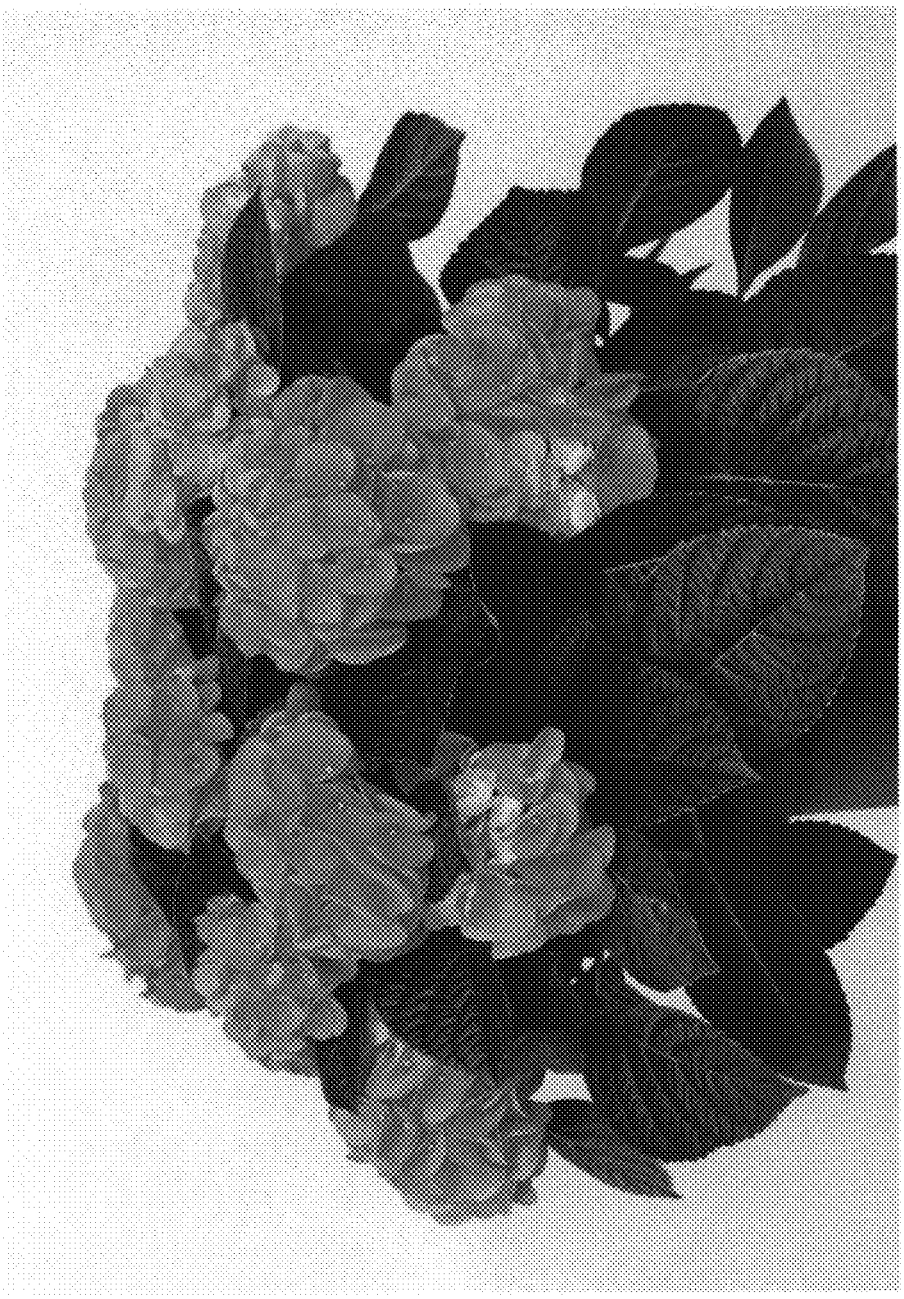

Botanical designation: *Hydrangea macrophylla.*
Cultivar denomination: 'HIMEA'.

STATEMENT REGARDING PRIOR DISCLOSURES BY INVENTOR/APPLICANT & ASSIGNEE

An European Community Plant Breeder's Rights application for the instant plant was filed by the Applicant/Assignee of the instant application, Hi Breeding B.V. of De Lier, The Netherlands on Nov. 15, 2021, application number 2021/2936. Foreign priority is not claimed to this European Plant Breeder's Rights application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'HIMEA'.

The new *Hydrangea* plant is a product of a planned breeding program conducted by the Inventor in De Lier, The Netherlands. The objective of the breeding program is to create new sturdy and strong *Hydrangea* plants with attractive inflorescences and good postproduction longevity.

The new *Hydrangea* plant originated from a cross-pollination on Apr. 5, 2016 of a proprietary selection of *Hydrangea macrophylla* identified as code number 1452, not patented, as the female, or seed, parent with a proprietary selection of *Hydrangea macrophylla* identified as code number 1671, not patented, as the male, or pollen, parent. The new *Hydrangea* plant was discovered and selected as a single flowering plant from within the progeny of the stated cross-pollination in a controlled greenhouse environment in De Lier, The Netherlands on Apr. 12, 2018.

Asexual reproduction of the new *Hydrangea* plant by terminal vegetative cuttings since Jul. 12, 2018 in a controlled greenhouse environment in De Lier, The Netherlands has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HIMEA'. These characteristics in combination distinguish 'HIMEA' as a new and distinct *Hydrangea* plant:

1. Compact, upright and broadly outwardly spreading and mounding plant habit.
2. Moderately vigorous and moderate growth rate.
3. Freely branching habit.
4. Strong and sturdy stems.
5. Dark green-colored leaves.
6. Freely flowering habit.
7. Large and dense inflorescences with vivid purplish red-colored sterile flowers.
8. Good post-production longevity.

Plants of the new *Hydrangea* can be compared to plants of the female parent selection. Plants of the new *Hydrangea* differ primarily from plants of the female parent selection in growth habit as plants of the new *Hydrangea* are not as vigorous as plants of the female parent selection.

Plants of the new *Hydrangea* can be compared to plants of the male parent selection. Plants of the new *Hydrangea* differ primarily from plants of the male parent selection in stein strength as stems of plants of the new *Hydrangea* are sturdier than stems of plants of the male parent selection. In addition, sepals of sterile flowers of plants of the new *Hydrangea* are lighter in color than sepals of sterile flowers of plants of the male parent selection.

Plants of the new *Hydrangea* can be compared to plants of *Hydrangea macrophylla* 'HBA 202911', not patented. In side-by-side comparisons, plants of the new *Hydrangea* differ primarily from plants of 'HBA 202911' in the following characteristics:

1. Stems of plants of the new *Hydrangea* are sturdier than stems of plants of 'HBA 202911'.
2. Sepals of sterile flowers of plants of the new *Hydrangea* are lighter in color than sepals of sterile flowers of plants of 'HBA 202911'.

Plants of the new *Hydrangea* can also be compared to plants of *Hydrangea macrophylla* 'LAVBLAA', not patented. In side-by-side comparisons, plants of the new *Hydrangea* differ primarily from plants of 'LAVBLAA' in the following characteristics:

1. Stems of plants of the new *Hydrangea* are sturdier than stems of plants of 'LAVBLAA'.
2. Sepals of sterile flowers of plants of the new *Hydrangea* are lighter in color than sepals of sterile flowers of plants of 'LAVBLAA'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1) is a side perspective view of a typical flowering plant of 'HIMEA' grown in a container.

Figure 2:
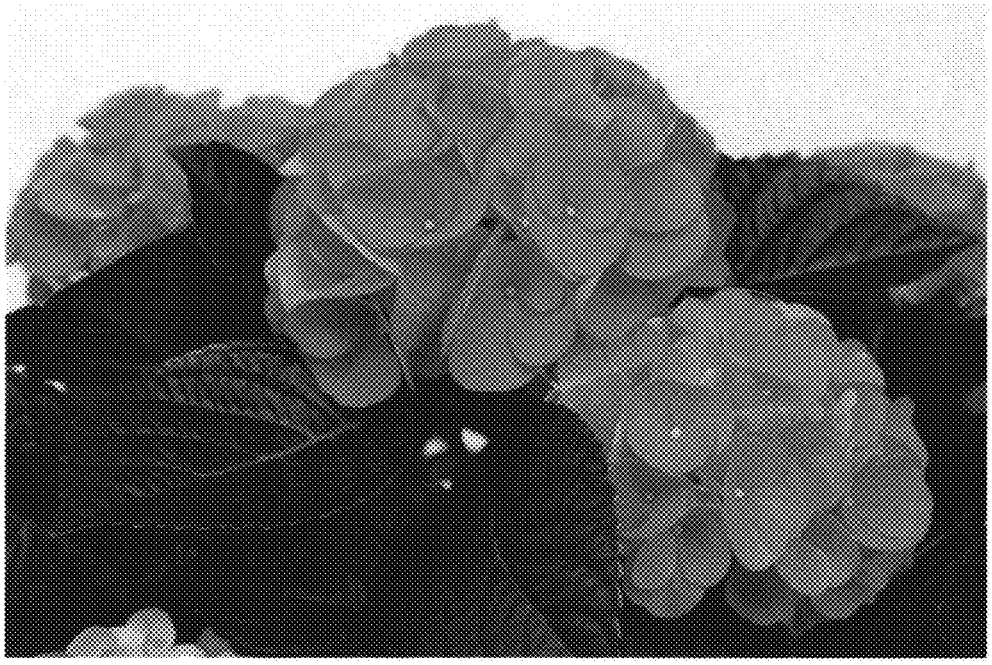

The photograph at the top of the second sheet (FIG. 2) is a close-up view of typical inflorescences of 'HIMEA'.

Figure 3:
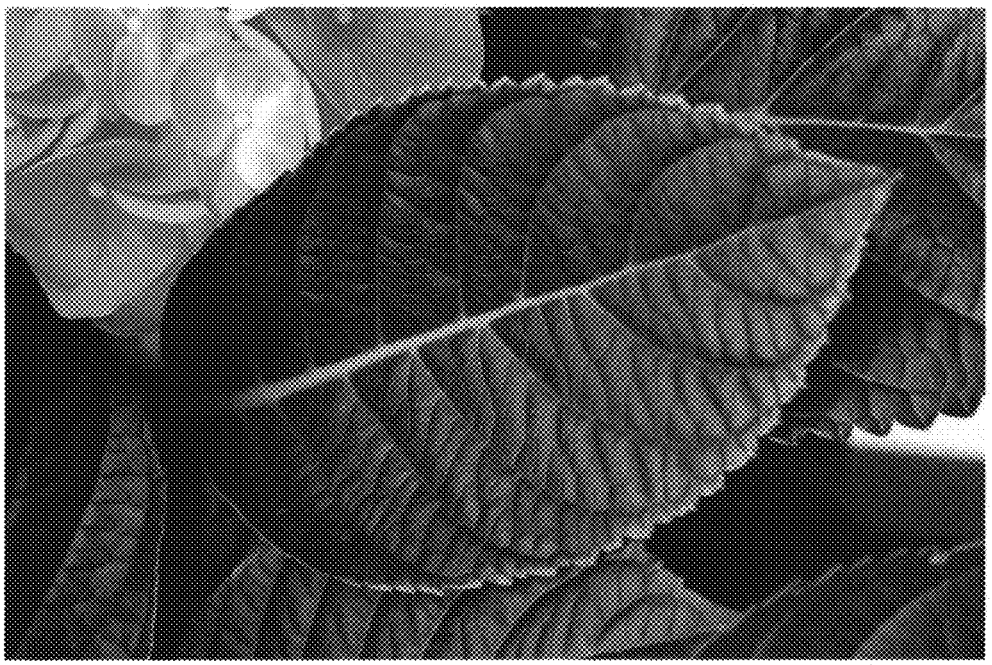

The photograph at the bottom of the second sheet (FIG. 3) is a close-up view of typical leaves of 'HIMEA'.

Figure 4:
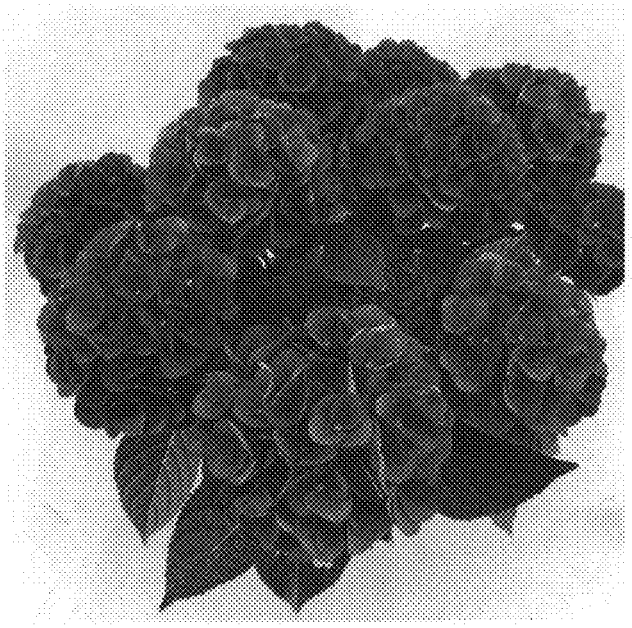

The photograph on the third sheet (FIG. 4) is a top perspective view of a typical flowering plant of 'HIMEA' that has been treated with aluminum sulfate, or "blued".

DETAILED BOTANICAL DESCRIPTION

Plants used in the aforementioned photographs and in the following description were grown during the late winter and early spring in 14-cm containers in a glass-covered greenhouse in De Lier, The Netherlands and under cultural practices typical of commercial *Hydrangea* production. During the production of the plants, day temperatures ranged from 20° C. to 35° C., night temperatures ranged from 10° C. to 22° C. and light levels averaged 4,000 lux. Plants of the new *Hydrangea* were pinched one time and were 18 months old when the photographs and description were taken. In the following description, color references are made to The Royal Horticultural Society Colour Chart, 2015 Edition, except where general terms of ordinary dictionary significance are used.

Botanical description: *Hydrangea macrophylla* 'HIMEA'.

Parentage:

*Female, or seed, patent.*—Proprietary selection of *Hydrangea macrophylla* identified as code number 1452, not patented.

*Male, or pollen, patent.*—Proprietary selection of *Hydrangea macrophylla* identified as code number 1671, not patented.

Propagation:

*Type cutting.*—By vegetative terminal cuttings.

*Time to initiate roots, summer.*—About twelve days at temperatures about 22° C.

*Time to initiate roots, winter.*—About two weeks at temperatures about 20° C.

*Time to produce a rooted young plant, summer.*—About four weeks at temperatures about 22° C.

*Time to produce a rooted young plant, winter.*—About one month at temperatures about 19° C.

*Root description.*—Medium in thickness, fibrous; typically white in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Compact, upright, broadly outwardly spreading and mounding plant habit; flattened globular in overall shape; strong and sturdy stems; moderately vigorous growth habit and moderate growth rate; about six months from propagation are required to produce small finished flowering plants.

*Plant height.*—About 29.2 cm.

*Plant diameter or area of spread.*—About 51.4 cm.

Lateral branch description:

*Branching habit.*—Freely branching habit with about 21 lateral branches per plant; pinching enhances lateral branch development.

*Length.*—About 16.4 cm.

*Diameter.*—About 5 mm.

*Internode length.*—About 4 cm.

*Strength.*—Strong, sturdy.

*Aspect.*—About 35° from vertical.

*Texture, developing and developed.*—Smooth, glabrous; becoming woody with subsequent development.

*Color, developing.*—Close to 138B and at the nodes, tinged with close to 183A to 183B.

*Color, fully developed.*—Close to 143A to 143B and at the nodes, tinged with close to a blend of 183A and N186C; when woody, close to 199A to 199B and N199B.

*Lenticels.*—Density: Sparse. Length: About 2 mm. Diameter: About 0.5 mm. Color: Close to a blend of 183A and N186C.

Leaf description:

*Arrangement.*—Opposite, simple.

*Length.*—About 11.4 cm.

*Width.*—About 6.9 cm.

*Shape.*—Ovate to broadly ovate and elliptic.

*Apex.*—Apiculate.

*Base.*—Attenuate.

*Margin.*—Coarsely crenate-serrate.

*Texture, upper and lower surfaces.*—Slightly rugose, glabrous.

*Venation pattern.*—Pinnate.

*Color.*—Developing leaves, upper surface: Close to 143A. Developing leaves, lower surface: Close to a blend of 143A and 144A. Fully developed leaves, upper surface: Darker than a blend of 147A and N189A; venation, close to 145A. Fully developed leaves, lower surface: Close to 147B; venation, close to 146C.

*Petioles.*—Length: About 2.4 cm. Diameter: About 4 mm. Texture and luster, upper surface: Smooth, glabrous; slightly glossy. Texture and luster, lower surface: Smooth, glabrous; moderately glossy. Color, upper surface: Close to a blend of 145A and 146C. Color, lower surface: Close to 146C.

Flower description:

*Flower type and habit.*—Showy rotate sterile flowers and small, inconspicuous rotate fertile flowers arranged on mophead-type terminal panicles; panicles flattened globular in shape; sterile flowers face upright to outwardly and fertile flowers mostly upright.

*Fragrance.*—None detected.

*Natural flowering season.*—In the garden, plants flower continuously from the late spring to late summer in The Netherlands; flower dormancy can be broken with a cold storage treatment.

*Flower longevity.*—Good postproduction longevity; sterile flowers maintain good substance for about six weeks on the plant, sterile flowers persistent; fertile flowers last for a few days on the plant, fertile flowers not persistent.

*Quantity of flowers.*—Freely flowering habit; about 120 sterile flowers per panicle and about 50 fertile flowers per panicle.

*Panicle height.*—About 7.8 cm.

*Panicle diameter.*—About 13 cm.

*Panicle peduncles.*—Length: About 3 cm. Diameter: About 3 mm. Strength: Strong. Aspect: Primary peduncles, mostly erect; lateral peduncles, about 45° from primary peduncle axis. Texture: Densely pubescent. Color: Close to 186D tinged with close to 185B.

*Sterile flower buds.*—Length: About 9 mm. Diameter: About 1.5 cm. Shape: Irregular and broadly cup-shaped. Color: Close to a blend of 150D and 155C; towards the apex, close to 62B.

*Fertile flower buds.*—Length: About 5 mm. Diameter: About 4 mm. Shape: Broadly obovate. Color: Close to 63C and 160C.

*Sterile flower diameter.*—About 3.3 cm to 4.4 cm.

*Sterile flower depth (height).*—About 1.4 cm to 2.1 cm.

*Fertile flower diameter.*—About 6 mm.

*Fertile flower depth (height).*—About 6 mm.

*Petals, sterile flowers.*—Quantity and arrangement: Four in a single whorl. Length: About 3 mm. Width: About 1.75 mm. Shape: Ovate, concave. Apex: Acute. Base: Cuneate. Margin: Entire. Texture and luster, upper and lower surfaces: Smooth, glabrous; matte. Color: When opening and fully opened, upper surface: Close to 65A and towards the margins, close to 69C; color does not change with subsequent development. When opening and fully opened, lower surface: Close to 68B; color does not change with subsequent development.

*Petals, fertile flowers.*—Quantity and arrangement: Five in a single whorl. Length: About 3 mm. Width: About 1.75 mm. Shape: Ovate, concave. Apex: Acute. Base: Cuneate. Margin: Entire. Texture and luster, upper and lower surfaces: Smooth, glabrous; matte. Color: When opening and fully opened, upper surface: Close to 65A and towards the margins, close to 69C; color does not change with subsequent development. When opening and fully opened, lower surface: Close to 68B; color does not change with subsequent development.

*Sepals, sterile flowers.*—Quantity and arrangement: Typically four, or occasionally three or five, in a single whorl; strongly imbricate. Length: About 1.8 cm to 2.3 cm. Width: About 1.8 cm to 3.3 cm. Shape: Reniform to roughly rhomboidal, slightly concave. Apex: Rounded to retuse. Base: Broadly cuneate to truncate. Margin: Entire; coarsely undulate. Texture and luster, upper and lower surfaces: Smooth, glabrous; matte. Color: When opening, upper surface: Close to 63B flushed with close to 63A. When opening, lower surface: Close to 64D. Fully opened, upper surface: Close to 61C fading lighter towards the margins and apex; with subsequent development, color becoming closer to 63B; when treated with aluminum sulfate or "blued", color becoming closer to 96A. Fully opened, lower surface: Close to between 63B and 63C; venation, close to 63A; with subsequent development, color becoming closer to a blend of 61D and 63B with venation, close to 63A; when treated with aluminum sulfate or "blued", color becoming closer to 96B.

*Sepals, fertile flowers.*—Quantity and arrangement: Five in a single whorl. Length: About 1 mm. Width: About 1.5 mm. Shape: Broadly deltoid. Apex: Acute. Base: Cuneate. Margin: Entire. Texture and luster, upper and lower surfaces: Smooth, glabrous; matte. Color: When opening and fully opened, upper surface: Close to 63B and 63C; color does not change with subsequent development. When opening and fully opened, lower surface: Close to 63B and 63C; color does not change with subsequent development.

*Pedicels, sterile flowers.*—Length: About 1.7 cm. Diameter: About 1.5 mm. Strength: Moderately strong. Aspect: About 30° from main peduncle axis. Texture and luster: Densely pubescent; slightly glossy. Color: Close to 186C and 186D.

*Pedicels, fertile flowers.*—Length: About 0.3 mm. Diameter: About 0.1 mm. Strength: Moderately strong. Aspect: About 10° from vertical. Texture and luster: Moderately pubescent; matte. Color: Close to 186C.

*Reproductive organs, sterile flowers.*—Stamens: Quantity per flower: Eight. Filament length: About 2 mm. Filament color: Close to N155B. Anther shape: Broadly oblong. Anther length: About 1 mm. Anther color: Close to 202A. Pollen amount: Moderate. Pollen color: Close to 155A. Pistils: Pistil quantity per flower: Two, or occasionally, three. Pistil length: About 1 mm. Stigma shape: Club-shaped. Stigma color: Close to 76D. Style length: About 0.5 mm. Style color: Close to 76D. Ovary color: Close to 76D.

*Reproductive organs, fertile flowers.*—Stamens: Quantity per flower: Ten. Filament length: About 2.5 mm. Filament color: Close to 186D. Anther shape: Broadly oblong. Anther length: About 1 mm. Anther color: Close to 202A. Pollen amount: Moderate. Pollen color: Close to 155A. Pistils: Pistil quantity per flower: Three, or occasionally, four. Pistil length: About 1.5 mm. Stigma shape: Club-shaped. Stigma color: Close to N155B to N155C. Style length: About 1.2 mm. Style color: Close to 69D. Ovary color: Close to 65C.

*Seeds.*—To date, seed development has not been observed on plants of the new *Hydrangea.*

Pathogen & pest resistance: To date, plants of the new *Hydrangea* have not been observed to be resistant to pathogens and pests common to *Hydrangea* plants.

Temperature tolerance: Plants of the new *Hydrangea* have been shown to be suitable for USDA Hardiness Zones 5 through 9.

It is claimed:

1. A new and distinct *Hydrangea* plant named 'HIMEA' as illustrated and described.

* * * * *